United States Patent
Sabbah

(10) Patent No.: US 12,390,486 B2
(45) Date of Patent: Aug. 19, 2025

(54) METHOD FOR TREATING DIASTOLIC HEART FAILURE BY INHIBITING GALECTIN-3

(71) Applicant: Henry Ford Health System, Detroit, MI (US)

(72) Inventor: Hani N. Sabbah, Waterford, MI (US)

(73) Assignee: Henry Ford Health System, Detroit, MI (US)

( * ) Notice: Subject to any disclaimer, the term of this patent is extended or adjusted under 35 U.S.C. 154(b) by 964 days.

(21) Appl. No.: 17/367,957

(22) Filed: Jul. 6, 2021

(65) Prior Publication Data

US 2021/0330694 A1 Oct. 28, 2021

Related U.S. Application Data

(63) Continuation-in-part of application No. 15/877,733, filed on Jan. 23, 2018, now Pat. No. 11,077,137, which is a continuation of application No. 14/654,140, filed as application No. PCT/US2013/077169 on Dec. 20, 2013, now Pat. No. 9,907,814.

(60) Provisional application No. 61/740,018, filed on Dec. 20, 2012.

(51) Int. Cl.
*A61K 31/732* (2006.01)

(52) U.S. Cl.
CPC .................. *A61K 31/732* (2013.01)

(58) Field of Classification Search
CPC ................. A61K 31/732; A61K 9/00
USPC .......................................... 514/54
See application file for complete search history.

(56) References Cited

U.S. PATENT DOCUMENTS

| | | | |
|---|---|---|---|
| 5,514,666 A | 5/1996 | Cerda et al. | |
| 7,638,623 B2 | 12/2009 | Nilsson et al. | |
| 9,907,814 B2 * | 3/2018 | Sabbah | A61K 31/732 |
| 11,077,137 B2 * | 8/2021 | Sabbah | A61P 9/00 |
| 2005/0032673 A1 | 2/2005 | John et al. | |
| 2006/0148712 A1 | 7/2006 | Liu et al. | |
| 2008/0213786 A1 | 9/2008 | Hurez et al. | |
| 2011/0294755 A1 * | 12/2011 | Eliaz | A61P 35/04 514/54 |
| 2012/0214818 A1 * | 8/2012 | Dudley | A61K 31/495 514/252.12 |
| 2013/0029955 A1 * | 1/2013 | Muntendam | A61K 31/00 435/7.1 |

FOREIGN PATENT DOCUMENTS

| | | |
|---|---|---|
| CA | 2435363 A1 | 7/2002 |
| CA | 2428473 C | 11/2012 |
| CA | 2521649 C | 5/2013 |
| EP | 2424873 | 11/2010 |
| EP | 1751171 B1 | 9/2011 |
| EP | 2620443 A1 | 7/2013 |
| EP | 2297174 B1 | 7/2015 |
| WO | 02100343 A2 | 12/2002 |
| WO | 03000195 A2 | 1/2003 |
| WO | 2005095463 A1 | 10/2005 |
| WO | 2005113569 A1 | 12/2005 |
| WO | 2008073817 A2 | 6/2008 |
| WO | 2008112559 A1 | 9/2008 |
| WO | 2013103984 A1 | 7/2013 |

OTHER PUBLICATIONS

Yu et al., Circ Heart Fail 2013, 6, 107-117.*
Wai et al., "Comparing biosorbent ability of modified citrus and durian rind pectin", Carbohydrate Polymers 79 (2010) 584-589.
Extended European Search Report for Application No. 13864237.6, dated Jun. 27, 2016, 6 pages.
Calvier et al., "Galectin-3 Mediates Aldosterone-Induced Vascular Fibrosis", Arterioscler Thromb Vasc Biol, Jan. 2013, 16 pages.
Yu et al., "Genetic and Pharmacological Inhibition of Galectin-3 Prevents Cardiac Remodeling by Interfering With Myocardial Fibrogenesis", Circ Heart Fail, Jan. 2013, 32 pages.

* cited by examiner

*Primary Examiner* — Ganapathy Krishnan
(74) *Attorney, Agent, or Firm* — Brooks Kushman P.C.

(57) ABSTRACT

A method for treating diastolic heart failure (heart failure with preserved ejection fraction (HFpEF)) in a subject in need thereof is provided including administering a therapeutically effective amount of a galectin-3 inhibitor to the subject.

9 Claims, 1 Drawing Sheet

METHOD FOR TREATING DIASTOLIC HEART FAILURE BY INHIBITING GALECTIN-3

CROSS-REFERENCE TO RELATED APPLICATIONS

This application is a continuation-in-part of U.S. application Ser. No. 15/877,733 filed Jan. 23, 2018, which is a continuation of U.S. application Ser. No. 14/654,140 filed Jun. 19, 2015, now U.S. Pat. No. 9,907,814, which is U.S. National Phase of PCT/US2013/077169 filed Dec. 20, 2013, which, in turn, claims the benefit of U.S. provisional application Ser. No. 61/740,018 filed Dec. 20, 2012, the disclosures of which are hereby incorporated in their entirety by reference herein.

TECHNICAL FIELD

Embodiments relate to treating diastolic heart failure by inhibiting galectin-3.

BACKGROUND

Heart failure (HF) involves an impairment in the ability of the heart to fill with and/or eject blood. Regardless of etiology, HF is associated with the accumulation of connective tissue termed "reactive interstitial fibrosis" in the interstitial compartment of the myocardium. Interstitial fibrosis can, in turn, have an adverse impact on the myocardium by 1) increasing oxygen diffusion distance and, therefore, lead to myocardial hypoxia; 2) reducing capillary density and, therefore, influence coronary perfusion and 3) increasing myocardial stiffness (reduce compliance) and, in doing so, reduce left ventricular relaxation and filling, and increase myocardial oxygen consumption. Reducing the burden of interstitial fibrosis, therefore, is a key therapeutic goal in HF.

While many therapies exist for treating systolic HF, the disease continues to claim the lives of many Americans and people worldwide. Even with optimal medical therapy, once diagnosed, systolic HF progressively worsens. Patients with advanced HF have a mortality rate of nearly 50% per year. Diastolic HF is a condition whereby the patient develops all the symptoms of systolic HF except that the systolic function of the left ventricle is not depressed, as is typical of systolic HF. In contrast to systolic HF, there are no known therapies for diastolic HF, even though this form of the disease affects nearly 40% of the entire HF population which, in the US, is nearly 6 million people. Identifying effective therapies to treat diastolic HF is a major unmet need in the United States and worldwide.

SUMMARY

In one or more embodiments, a method for treating heart failure with preserved ejection fraction (HFpEF) in a subject in need thereof includes administering a therapeutically effective amount of a galectin-3 inhibitor to the subject.

In one or more embodiments, a method for treating a subject exhibiting at least one symptom of heart failure with preserved ejection fraction (HFpEF) includes administering a therapeutically effective amount of an inhibitor of galectin-3 to the subject.

In one or more embodiments, a method for treating diastolic heart failure in a subject with a left ventricular ejection fraction of greater than about 45% includes administering a therapeutically effective amount of N-acetyl-D-lactosamine (LacNAc) to the subject.

DETAILED DESCRIPTION

Figure 1:
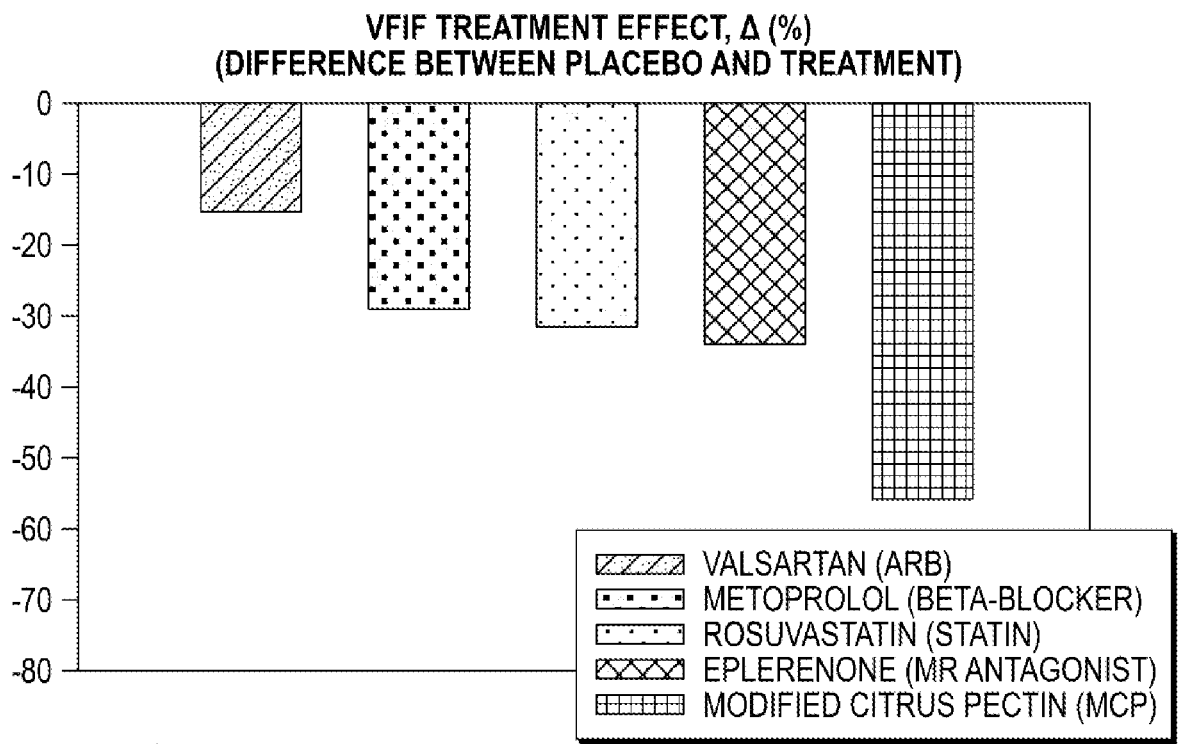
FIG. 1 is a graph illustrating the difference between Modified Citrus Pectin (MCP) and other prototypical drugs tested in a canine model of HF with respect to volume fraction of interstitial fibrosis (VFIF)

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "subject" refers to a human or animal, including all mammals such as primates (particularly higher primates), sheep, dog, rodents (e.g., mouse or rat), guinea pig, goat, pig, cat, rabbit, and cow.

The term "treating" includes any effect (e.g., lessening, reducing, eliminating, etc.) that results in the improvement of the condition.

The term "pharmaceutically acceptable" includes molecular entities and compositions that do not produce an adverse, allergic, or other unwanted reaction when administered to a subject.

The term "pharmaceutically acceptable carrier" includes any and all solvents, coatings, and the like that are compatible with pharmaceutical administration. The use of such agents for pharmaceutically active substances is well known in the art.

The term "pharmaceutical composition" includes a composition comprising at least one compound as disclosed herein formulated together with one or more pharmaceutically acceptable carriers.

The term "therapeutically effective amount" refers to the amount of the compound that will elicit the biological or medical response of a tissue, system or subject that is being sought. The compounds are administered in therapeutically effective amounts to treat a disease. Alternatively, a therapeutically effective amount of a compound is the quantity required to achieve a desired therapeutic effect.

Subjects having diastolic HF (heart failure with preserved ejection fraction: HFpEF) are identified as follows. In diastolic HP, the systolic function of the left ventricle is not depressed, as is typical of systolic HF. Instead, the left ventricle cannot fill properly. The poor filling may be due to multiple factors such as poor calcium cycling and left ventricular hypertrophy, but is believed to also be due largely to interstitial fibrosis that causes decreased left ventricular compliance. In patients with diastolic HF, the left ventricle tends to be smaller than that of a normal subject without diastolic HF, with hypertrophied walls and poor filling.

A patient (subject) presents with symptoms of acute heart failure (i.e., shortness of breath and pulmonary edema), but upon conducting tests, the patient is found to have a left ventricular ejection fraction greater than about 45%. Thus, the diagnosis is heart failure with preserved ejection fraction (HFpEF), or diastolic HF. This is in contradistinction from heart failure with reduced ejection fraction (HFrEF), or systolic HF, whereby the patient has the same symptoms but left ventricular ejection fraction is reduced usually below 35%.

In a systolic HF patient, heart failure results from inability of the left ventricle to eject blood to meet the demands of the body. The ventricle can fill normally but cannot eject the blood normally. This is caused by an inability of the ventricle to contract normally. As a result, the ventricle will get larger and larger and, in this way, a small amount of contraction from a larger volume leads to more blood being ejected. However, as the ventricle continues to dilate, stresses on the muscle continue to mount, causing negative effects on muscle cells, including the death of muscle cells. Thus, patients with very dilated left ventricles have poor prognosis. In fact, in systolic HF patients, the size of the ventricle is a very sensitive indicator of mortality and worsening heart failure (morbidity).

In contrast, in diastolic HF patients, the ventricle is usually very small (smaller than in normal, control subjects without diastolic HF). The ventricle can eject normally, but is unable to fill normally, as filling is poor due to stiff muscle, etc. As a result, the left ventricle in both systolic HF and diastolic HF is incapable of meeting the needs of the body to eject normal amounts of blood with each heartbeat, so patients develop the same symptoms but for different reasons. In systolic HF, the contraction is abnormal but the relaxation (filling) is normal, whereas in diastolic HF, the contraction is normal but the relaxation (filling) is abnormal. From a therapy standpoint, we aim to improve contraction in systolic HF, but in diastolic HF we aim to improve filling or relaxation. In diastolic HF, evidence of improved filling is achieved by increasing the size of the left ventricle.

Importantly, current therapies for systolic HF are not effective for treating diastolic HF because all these therapies have been developed for systolic HF with the objective of improving contraction of the muscle and preventing the ventricle from continuing to enlarge, the exact opposite of what is needed for patients who have diastolic HF. An increase in left ventricular size is detrimental to the patient with systolic HF for the reasons described above.

The development of the diastolic HF is also associated with an increase in the volume fraction of interstitial fibrosis in the left ventricular wall. Embodiments disclosed herein target inhibition of galectin-3 as a therapeutic approach to reducing interstitial fibrosis. Reduction of interstitial fibrosis in diastolic HF patients should increase left ventricular compliance and, in doing so, increase left ventricular size and improve left ventricular function. This should improve left ventricular filling and emptying and, in doing so, relieve symptoms of diastolic HF such as shortness of breath and pulmonary congestion.

Therefore, a method for treating diastolic HF in a subject by inhibiting galectin-3 is described herein. Various compositions comprising a compound that binds to galectin-3 to inhibit its activity are disclosed, wherein the composition may be administered to a subject. In another aspect, a method of treating a subject at risk of developing diastolic HF by inhibiting galectin-3 is provided. In some cases, a compound capable of binding to galectin-3 may reduce the risk of a subject developing diastolic HF as compared to an untreated subject. A subject at risk of developing diastolic HF may not yet present with symptoms necessary for a diagnosis of diastolic HF, but may have left ventricular parameters such as, for example, fibrosis, size, ejection fraction, and end-systolic and end-diastolic volumes which deviate from normal control subjects and trend toward the values associated with a diagnosis of diastolic HF.

Galectin-3 is a member of the lectin family, of which 14 mammalian galectins have been identified. Galectin-3 is approximately 30 kDa and, like all galectins, contains a carbohydrate-recognition-binding domain (CRD) of about 130 amino acids that enable the specific binding of β-galactosides. Galectin-3 is encoded by a single gene, LGALS3, located on chromosome 14, locus q21-q22. It is expressed in the nucleus, cytoplasm, mitochondrion, cell surface, and extracellular space. This protein has been shown to be involved in the following biological processes: cell adhesion, cell activation and chemoattraction, cell growth and differentiation, cell cycle, and apoptosis. Given galectin-3's broad biological functionality, it has been demonstrated to be involved in cancer, inflammation and fibrosis, heart disease, and stroke. Studies have also shown that the expression of galectin-3 is implicated in a variety of processes associated with HF, including myofibroblast proliferation, fibrogenesis, inflammation, and ventricular remodeling. Elevated levels of galectin-3 have been found to be significantly associated with higher risk of death in both acute decompensated HF and chronic HF populations.

A composition or compound that is capable of binding galectin-3, and therefore a galectin-3 inhibitor, may be administered to a subject identified with diastolic HF (HFpEF). Any suitable compound may be used. For example, in certain embodiments, the galectin-3 inhibitor may be a carbohydrate, such as a polysaccharide, a protein, a nucleic acid, or a small molecule. In one example, the galectin-3 inhibitor may comprise galactose. In some embodiments, a galectin-3 antibody may be used as an inhibitor of galectin-3. Specific examples of the many galectin-3 inhibitors listed above are well known in the art.

In one example, the galectin-3 inhibitor may comprise a pectin, modified pectin, or pectin derivative. Pectins are polysaccharides from plant cell walls, especially from apple and citrus fruits. A pectin used may be a full-length pectin or may be a pectin fragment. Pectin fragments of interest are capable of binding to galectin-3. It may be advantageous to purify a pectin fragment by any suitable method. In some embodiments, a pectin may have a molecular weight of between about 50 kDa and about 150 kDa, between about 60 kDa and about 130 kDa, between about 50 kDa and about 100 kDa, between about 30 kDa and about 60 kDa, between about 10 kDa and about 50 kDa, between about 10 kDa and about 30 kDa, between about 5 kDa and about 20 kDa, or between about 1 kDa and about 10 kDa.

The product Modified Citrus Pectin (MCP) may be used as a galectin-3 inhibitor. MCP is different from other pectins, as it is modified from organic citrus pectin to reduce the molecular weight of the pectin molecule, such as to between about 10 kDa and about 30 kDa or between about 5 kDa and about 20 kDa. Although pectins are not digestible by humans, MCP is altered to increase its absorbability. MCP is most often used as an adjuvant to cancer therapy to support prevention of metastasis. Pectins, including MCP, have also been investigated for possible cardiovascular supporting benefits, including lowering cholesterol and reducing atherosclerosis and have been shown to reduce the volume fraction of fibrous tissue and to partially inhibit galectin-3. MCP has been shown to reduce galectin-3 expression and disease severity in experimental acute kidney injury in mice. MCP can bind to the galectin-3 carbohydrate recognition domain, thereby predominantly antagonizing functions linked to this role.

Galectin-3 inhibitors unrelated to pectins may also be used. In one example, N-acetyl-D-lactosamine (LacNAc: CAS 32181-59-2), LacNAc derivatives, or other similar disaccharides or oligosaccharides may be selected. LacNAc is a disaccharide with a molecular weight of 383.35 that is one of the natural oligosaccharides found in breast milk. Since the discovery of galectin-3 as a ligand for poly-N-acetyllactosamine compounds, the interaction between N-acetyl-D-lactosamine and galectin-3 has been studied extensively. Research into the binding to and inhibition of galectin-3 by LacNAc included preclinical studies where LacNAc was administered.

Additional inhibitors may be identified, for example, by screening compounds suspected of having galectin-3 binding properties. In some embodiments, a compound capable of binding to galectin-3 may be selected based on a desired pharmacological half-life. For example, in some embodiments, a compound capable of binding to galectin-3 may have a pharmacological half-life of between about 0.5 hours and about 12 hours. In some embodiments, binding of a compound to galectin-3 may inhibit an activity of galectin-3 or may reduce the expression level of galectin-3.

In some embodiments, pharmaceutical compositions comprising a compound capable of binding galectin-3 formulated together with a pharmaceutically acceptable carrier may be provided. Pharmaceutical compositions may be used, for example, in a solid, semi-solid, or liquid form, which contains one or more of the compounds as an active ingredient. The compound is included in the pharmaceutical composition in an amount sufficient to produce the desired effect upon the condition of the subject.

A composition or compound for inhibiting galectin-3 may be administered, for example, orally, subcutaneously, topically, intravenously, intramuscularly or by inhalation. The compositions may be administered to subjects in need of such treatment in therapeutically effective amounts. The galectin-3 inhibitors can be dosed, for example, based on the weight of the subject or as a fixed dose. In one example, a dose of MCP can be between about 1 g and 10 g, between about 3 g and 7 g, or about 5 g. It is understood that the dose required will vary from subject to subject, not only with the particular compound or composition and potency selected, but also with the route of administration, the age and condition of the subject, concurrent medication used by the subject, and other like factors.

Treatment can be continued for as long or as short of a period as desired. The compositions may be administered at a frequency of, for example, one to four or more times per day. A suitable treatment period can be, for example, at least about one week, at least about two weeks, at least about one month, at least about three months, at least about six months, at least about one year, or indefinitely. A treatment period may be complete when a desired result is achieved, such as at least a partial alleviation of symptoms of a condition.

In certain cases, treatment may be monitored by determining the level of galectin-3 in a subject. Determining the level of galectin-3 in a subject may comprise obtaining a biological sample (e.g., blood) from the subject. In some embodiments, a subject may be identified for treatment by the level of galectin-3 in the blood (e.g., plasma) of the subject, for example, when the subject has an elevated level of galectin-3 in the plasma compared to a healthy, control subject. However, an elevated level of galectin-3 in the blood stream is not required as a condition for proceeding with therapy for diastolic HF as disclosed herein.

In some embodiments, a symptom of diastolic HF (HFpEF) may be at least partially alleviated. Alleviating a symptom may refer to at least partially inhibiting or reducing a symptom, a reduction in the frequency of occurrence of a symptom, and/or a slowing of the development of a symptom.

The method disclosed herein for treating diastolic HF by inhibiting galectin-3 at least partially alleviates a symptom of diastolic HF and therefore provides several therapeutic advantages. Inhibition of galectin-3 reduces fibrosis, which is associated with improved left ventricular systolic function. In some embodiments, fibrosis can be reduced at least about 50%, at least about 40%, at least about 30%, at least about 20%, or at least about 10% after treatment compared to before treatment. Inhibition of galectin-3 increases left ventricular size evidenced by increased left ventricular end-systolic and end-diastolic volumes. While this is not a desirable feature for systolic HF, an increase in left ventricular size along with improvement of left ventricular function are both desirable features for treatment of diastolic HF, so as to result in better filling of the left ventricle with blood. Inhibition of galectin-3 improves left ventricular systolic function as evidenced by increased left ventricular ejection fraction. In diastolic dysfunction, a greater portion of end-diastolic volume results from late filling rather than early filling. Therefore, the ratio of the early (E) to late (A) peak ventricular filling velocities, or the E/A ratio, is reduced in diastolic dysfunction. Inhibition of galectin-3 improves left ventricular diastolic function as evidenced by increased E/A and Ei/Ai (ratio of early to late integrated velocity over time. These are all beneficial effects that one seeks to achieve in subjects with diastolic HF. Treatment may be monitored at any time by assessing any of the above-described left ventricular parameters.

The following examples illustrate the various embodiments of the present invention. More specifically, experimental studies with two heterogeneous galectin-3 ligands have demonstrated equivalent results in support of the disclosed method of treating HFpEF by administering a therapeutically effective amount of a galectin-e inhibitor to a subject in need thereof. Those skilled in the art will recognize many variations that are within the spirit of the present invention and scope of the claims.

EXAMPLE 1

Galectins are a family of galactoside-binding proteins, and hence readily available complex carbohydrates rich in galactoside residues were tested as inhibitors. The most abundant and low-cost galectoside-rich material available is citrus pectin—the soluble fiber derived from the white material (albedo) of orange, lemon, lime and grapefruit. It is an abundant by-product of juice production and generally used as animal feed or fertilizer. Although citrus pectin (CP) is effective as a galectin-3 inhibitor, the depolymerizing of CP by pH modification yields a mixture of smaller fragments generally known as modified citrus pectin (MCP).

MCP was chosen for this experiment to illustrate this effect and benefit. MCP was commercially available as supplement for human use under the brand name Pectasol (Ecougenics, Santa Rosa, California).

In a study in dogs with HF, the hypothesis was tested that inhibition of galectin-3 will markedly inhibit interstitial fibrosis in dogs (n=3) with microembolization-induced HF. In this dog model of HF, the development of the disease is associated with an increase in the volume fraction of interstitial fibrosis in the left ventricular wall from a normal level of 3.5% (connective tissue) to as high as 25%. Dogs were treated for 3 months with daily oral administration of 5 g MCP.

The results of the study in 3 dogs showed that monotherapy with MCP reduced reactive interstitial fibrosis by nearly 55% compared to historical controls. This is markedly higher than any other drug currently used in the treatment of HF. FIG. 1 illustrates the difference between MCP and other prototypical drugs tested in this canine model of HF with respect to volume fraction of interstitial fibrosis (VFIF). This reduction in fibrosis was also associated with improved LV systolic function. In the 3 dogs treated, LV ejection fraction increased from near 25% at baseline to 28% at 3 months into the therapy. In addition, there was an increase in LV end-diastolic volume from near 63 ml to near 75 ml. Detailed results are given in Tables 1-11 below.

TABLE 1

Left Ventricular End-Diastolic Volume (ml)

| Dog # | Pre | 6 weeks | Post | Delta |
|---|---|---|---|---|
| 12-004 | 63 | 73 | 77 | 14 |
| 12-005 | 73 | 80 | 86 | 13 |
| 12-029 | 54 | 64 | 63 | 9 |
| Mean | 63 | 72 | 75 | 12 |
| STD | 9.5 | 8.0 | 11.6 | 3 |
| SEM | 5.5 | 4.6 | 6.7 | 2 |

TABLE 2

Left Ventricular End-Systolic Volume (ml)

| Dog # | Pre | 6 weeks | Post | Delta |
|---|---|---|---|---|
| 12-004 | 45 | 48 | 50 | 5 |
| 12-005 | 57 | 62 | 67 | 10 |
| 12-029 | 41 | 48 | 46 | 5 |
| Mean | 48 | 53 | 54 | 7 |
| STD | 8.3 | 8.1 | 11.2 | 3 |
| SEM | 4.8 | 4.7 | 6.4 | 2 |

TABLE 3

Left Ventricular Ejection Fraction (%)

| Dog # | Pre | 6 weeks | Post | Delta |
|---|---|---|---|---|
| 12-004 | 29 | 34 | 35 | 6 |
| 12-005 | 22 | 23 | 22 | 0 |
| 12-029 | 24 | 25 | 27 | 3 |
| Mean | 25 | 27 | 28 | 3 |
| STD | 3.4 | 6.2 | 6.6 | 3 |
| SEM | 2.0 | 3.6 | 3.8 | 2 |

TABLE 4

Stroke Volume (ml)

| Dog # | Pre | 6 weeks | Post | Delta |
|---|---|---|---|---|
| 12-004 | 18 | 25 | 27 | 9 |
| 12-005 | 16 | 18 | 19 | 3 |
| 12-029 | 13 | 16 | 17 | 4 |
| Mean | 16 | 20 | 21 | 5 |
| STD | 2.5 | 4.7 | 5.3 | 3 |
| SEM | 1.5 | 2.7 | 3.1 | 2 |

TABLE 5

Cardiac Output (L/min)

| Dog # | Pre | 6 weeks | Post | Delta |
|---|---|---|---|---|
| 12-004 | 0.02 | 0.03 | 0.03 | 0.01 |
| 12-005 | 0.02 | 0.02 | 0.02 | 0.00 |
| 12-029 | 0.01 | 0.02 | 0.02 | 0.00 |
| Mean | 0.02 | 0.02 | 0.02 | 0.01 |
| STD | 0.00 | 0.00 | 0.01 | 0.00 |
| SEM | 0.00 | 0.00 | 0.00 | 0.00 |

TABLE 6

Peak E (cm/sec)

| Dog # | Pre | 6 weeks | Post | Delta |
|---|---|---|---|---|
| 12-004 | 67.0 | 63.0 | 37.0 | −30 |
| 12-005 | 60.0 | 43.0 | 55.0 | −5 |
| 12-029 | 43.0 | 46.0 | 41.0 | −2 |
| Mean | 56.7 | 50.7 | 44.3 | −12.3 |
| STD | 12.3 | 10.8 | 9.5 | 15.4 |
| SEM | 7.1 | 6.2 | 5.5 | 8.9 |

TABLE 7

Peak A (cm/sec)

| Dog # | Pre | 6 weeks | Post | Delta |
|---|---|---|---|---|
| 12-004 | 28.0 | 24.0 | 17.0 | −11 |
| 12-005 | 34.0 | 21.0 | 21.0 | −13 |
| 12-029 | 29.0 | 25.0 | 17.0 | −12 |
| Mean | 30.3 | 23.3 | 18.3 | −12.0 |
| STD | 3.2 | 2.1 | 2.3 | 1.0 |
| SEM | 1.9 | 1.2 | 1.3 | 0.6 |

TABLE 8

Peak E/A

| Dog # | Pre | 6 weeks | Post | Delta |
|---|---|---|---|---|
| 12-004 | 2.4 | 2.6 | 2.2 | −0.22 |
| 12-005 | 1.8 | 2.0 | 2.6 | 0.85 |
| 12-029 | 1.5 | 1.8 | 2.4 | 0.93 |
| Mean | 1.88 | 2.17 | 2.40 | 0.52 |
| STD | 0.47 | 0.41 | 0.22 | 0.64 |
| SEM | 0.27 | 0.23 | 0.13 | 0.37 |

TABLE 9

Ei (cm)

| Dog # | Pre | 6 weeks | Post | Delta |
|---|---|---|---|---|
| 12-004 | 7.0 | 7.2 | 3.8 | −3.2 |
| 12-005 | 3.0 | 3.3 | 3.5 | 0.5 |
| 12-029 | 3.7 | 4.5 | 4.5 | 0.8 |
| Mean | 4.6 | 5.0 | 3.9 | −0.6 |
| STD | 2.1 | 2.0 | 0.5 | 2.2 |
| SEM | 1.2 | 1.2 | 0.3 | 1.3 |

TABLE 10

Ai

| Dog# | Pre | 6 weeks | Post | Delta |
|---|---|---|---|---|
| 12-004 | 1.9 | 1.5 | 0.7 | −1.2 |
| 12-005 | 0.9 | 1.0 | 0.9 | 0 |
| 12-029 | 1.1 | 1.2 | 1.0 | −0.1 |
| Mean | 1.3 | 1.2 | 0.9 | −0.4 |
| STD | 0.5 | 0.3 | 0.2 | 0.7 |
| SEM | 0.3 | 0.1 | 0.1 | 0.4 |

TABLE 11

Ei/Ai

| Dog# | Pre | 6 weeks | Post | Delta |
|---|---|---|---|---|
| 12-004 | 3.7 | 4.8 | 5.4 | 1.74 |
| 12-005 | 3.3 | 3.3 | 3.9 | 0.56 |
| 12-029 | 3.4 | 3.8 | 4.5 | 1.14 |
| Mean | 3.46 | 3.95 | 4.61 | 1.15 |
| STD | 0.19 | 0.77 | 0.78 | 0.59 |
| SEM | 0.11 | 0.44 | 0.45 | 0.34 |

EXAMPLE 2

In order to illustrate that the effects observed with MCP apply to the entire class or spectrum of galectin-3 inhibitors, a small molecule galectin-3 inhibitor unrelated to pectins was used in a repeat experiment. The selected compound is N-acetyl-D-lactosamine (LacNAc: CAS 32181-59-2). Stated another way, in order to support that the observed inhibitory effect was mediated by binding to the carbohydrate recognition domain, the experiment described below was conducted using a disaccharide unrelated to pectins that was also known to bind and inhibit galectin-3.

In a study in dogs with HF, the hypothesis was tested that inhibition of galectin-3 will markedly inhibit interstitial fibrosis in dogs (n=3) with microembolization-induced HF. In this dog model of HF, the development of the disease is associated with an increase in the volume fraction of interstitial fibrosis in the left ventricular wall from a normal level of 3.5% (connective tissue) to as high as 25%. Dogs were treated for 3 months with daily oral administration of 115 mg of LacNAc.

Figure 2:
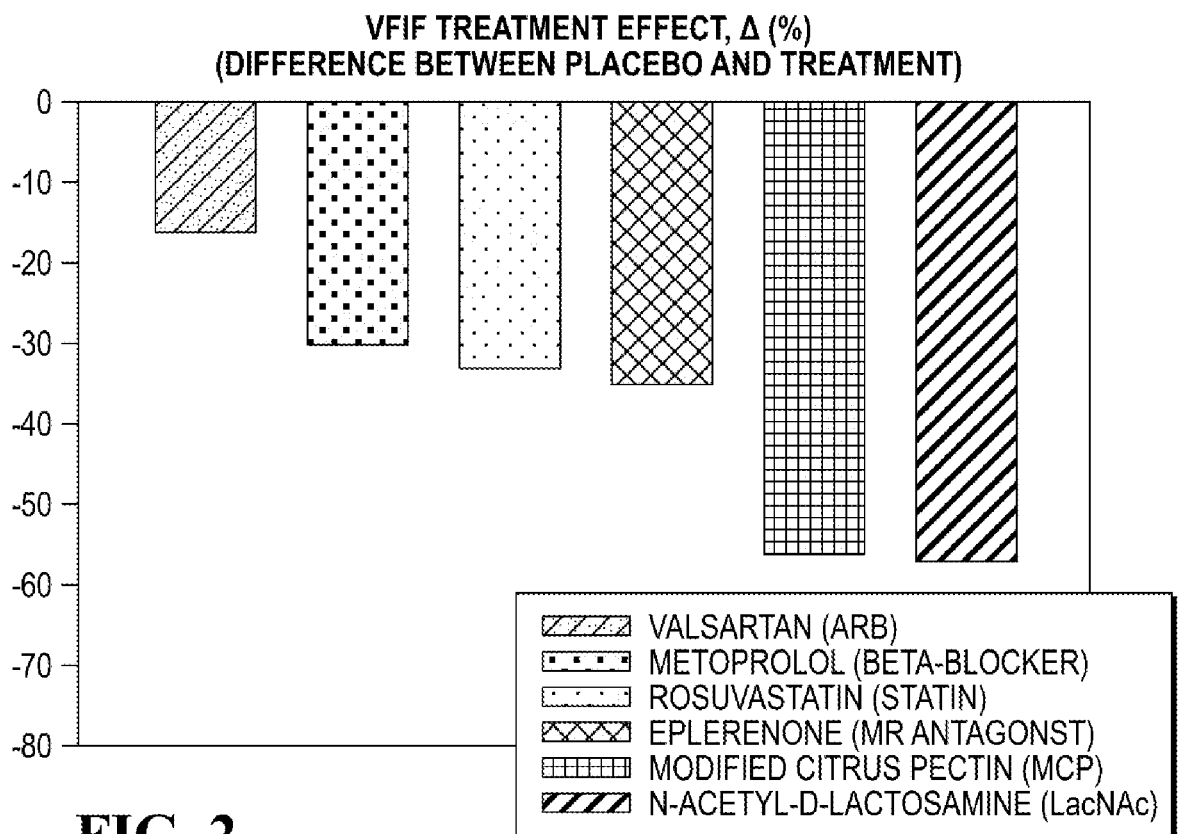
FIG. 2 is a graph illustrating the difference between MCP and N-acetyl-D-lactosamine (LacNAc) and other prototypical drugs tested in a canine model of HF with respect to volume fraction of interstitial fibrosis (VFIF).

The results of the study in 3 dogs showed that monotherapy with LacNAc reduced reactive interstitial fibrosis by nearly 57% compared to historical untreated controls that were matched to study dogs for LV ejection fraction, gender, and duration of heart failure. This finding is similar to that observed with MCP (Example 1), as illustrated in FIG. 2. This reduction of interstitial fibrosis was also associated with 1) improved LV relaxation as evidenced by improved indexes of LV relaxation, namely Ei/Ai, PE/PA and DT; 2) improved LV ejection fraction; 3) increased stroke volume and cardiac output; 4) increased capillary density; 5) decreased myocyte hypertrophy; and 6) increased oxygen diffusion. All of these findings support a marked improvement of LV function and cellular remodeling sought for treatment of HFpEF. Detailed results are given in Tables 12-27 below.

TABLE 12

Left Ventricular End-Diastolic Volume (ml)

| Dog# | PRE | 12 weeks |
|---|---|---|
| 18-048 | 53 | 57 |
| 18-050 | 50 | 53 |
| 19-003 | 64 | 62 |
| Mean | 56 | 57 |
| STD | 7 | 5 |
| SEM | 4 | 3 |

TABLE 13

Left Ventricular Fractional Area of Shortening (%)

| Dog # | PRE | 12 weeks |
|---|---|---|
| 18-048 | 26 | 31 |
| 18-050 | 36 | 41 |
| 19-003 | 23 | 29 |
| Mean | 28.3 | 33.7 |
| STD | 6.8 | 6 |
| SEM | 3.9 | 4 |

TABLE 14

Left Ventricular End-Systolic Volume (ml)

| Dog# | PRE | 12 weeks |
|---|---|---|
| 18-048 | 34 | 33 |
| 18-050 | 35 | 33 |
| 19-003 | 48 | 43 |
| Mean | 39 | 36 |
| STD | 8 | 6 |
| SEM | 5 | 3 |

TABLE 15

PE/PA

| Dog # | PRE | 12 weeks |
|---|---|---|
| 18-048 | 1.69 | 1.82 |
| 18-050 | 2.27 | 2.52 |
| 19-003 | 1.45 | 1.84 |
| Mean | 1.80 | 2.06 |
| STD | 0.42 | 0.40 |
| SEM | 0.24 | 0.23 |

TABLE 16

Left Ventricular Ejection Fraction (%)

| Dog# | PRE | 12 weeks |
|---|---|---|
| 18-048 | 36 | 42 |
| 18-050 | 30 | 38 |
| 19-003 | 25 | 31 |
| Mean | 30 | 37 |
| STD | 6 | 6 |
| SEM | 3 | 3 |

TABLE 17

Ei/Ai

| Dog # | PRE | 12 weeks |
|---|---|---|
| 18-048 | 3.25 | 4.26 |
| 18-050 | 3.85 | 4.43 |
| 19-003 | 1.85 | 3.25 |
| Mean | 2.98 | 3.98 |
| STD | 1.03 | 0.64 |
| SEM | 0.59 | 0.37 |

TABLE 18

Stroke Volume (ml)

| Dog# | PRE | 12 weeks |
|---|---|---|
| 18-048 | 19 | 24 |
| 18-050 | 15 | 20 |
| 19-003 | 16 | 19 |
| Mean | 17 | 21 |
| STD | 2 | 3 |
| SEM | 1 | 2 |

TABLE 19

DT (msec)

| Dog # | PRE | 12 weeks |
|---|---|---|
| 18-048 | 151 | 162 |
| 18-050 | 152 | 162 |
| 19-003 | 89 | 115 |
| Mean | 131 | 146 |
| STD | 36 | 27 |
| SEM | 21 | 16 |

TABLE 20

Cardiac Output (L/min)

| Dog # | PRE | 12 weeks |
|---|---|---|
| 18-048 | 1.63 | 2.02 |
| 18-050 | 1.22 | 1.80 |
| 19-003 | 1.38 | 1.67 |
| Mean | 1.41 | 1.83 |
| STD | 0.21 | 0.17 |
| SEM | 0.12 | 0.10 |

TABLE 21

Heart Rate (beats/min)

| Dog# | PRE | 12 weeks |
|---|---|---|
| 18-048 | 86 | 84 |
| 18-050 | 81 | 90 |
| 19-003 | 86 | 88 |
| Mean | 84 | 87 |
| STD | 3 | 3 |
| SEM | 2 | 2 |

TABLE 22

Systolic Aortic Pressure (mmHg)

| Dog# | PRE | 12 weeks |
|---|---|---|
| 18-048 | 87 | 88 |
| 18-050 | 85 | 90 |
| 19-003 | 88 | 88 |
| Mean | 87 | 89 |
| STD | 2 | 1 |
| SEM | 1 | 1 |

TABLE 23

Diastolic Aortic Pressure (mmHg)

| Dog# | PRE | 12 weeks |
|---|---|---|
| 18-048 | 61 | 60 |
| 18-050 | 61 | 67 |
| 19-003 | 64 | 62 |
| Mean | 62 | 63 |
| STD | 2 | 4 |
| SEM | 1 | 2 |

TABLE 24

Mean Aortic Pressure (mmHg)

| Dog# | PRE | 12 weeks |
|---|---|---|
| 18-048 | 72 | 72 |
| 18-050 | 72 | 76 |
| 19-003 | 75 | 73 |
| Mean | 73 | 74 |
| STD | 2 | 2 |
| SEM | 1 | 1 |

TABLE 25

Systemic Vascular Resistance
(dynes-sec-cm^-5)

| Dog # | PRE | 12 weeks |
|---|---|---|
| 18-048 | 3525 | 2857 |
| 18-050 | 4741 | 3378 |
| 19-003 | 4360 | 3493 |
| Mean | 4209 | 3243 |
| STD | 622 | 339 |
| SEM | 359 | 196 |

TABLE 26

N-Acetyl-D-lactosamine

| Dog # | VFRF (%) | VFIF (%) | Cap/mm$^2$ | ODD (μm) | MCSA μm$^2$ |
|---|---|---|---|---|---|
| 18-048 | 10.4 | 5.27 | 2989 | 9.18 | 373 |
| 18-050 | 13.6 | 5.27 | 2977 | 9.48 | 393 |
| 19-003 | 13.8 | 6.07 | 3042 | 9.11 | 418 |
| Mean | 12.6 | 5.54 | 3002 | 9.26 | 395 |
| STD | 1.9 | 0.46 | 34 | 0.20 | 22 |
| SEM | 1.1 | 0.27 | 20 | 0.12 | 13 |

TABLE 27

Historical Controls

| Dog # | VFRF (%) | VFIF (%) | Cap/mm$^2$ | ODD (μm) | MCSA μm$^2$ |
|---|---|---|---|---|---|
| D11-041 | 12.4 | 13.30 | 2060 | 13.38 | 535 |
| D11-087 | 13.6 | 13.36 | 2101 | 12.88 | 577 |
| D11-091 | 15.3 | 12.19 | 2029 | 13.03 | 613 |
| Mean | 13.8 | 12.95 | 2063 | 13.10 | 575 |
| STD | 1.5 | 0.66 | 36 | 0.25 | 39 |
| SEM | 0.8 | 0.38 | 21 | 0.15 | 22 |

Matched for EF, Gender, Duration of CHF
VFRF = LV volume fraction of replacement fibrosis
VFIF = LV Volume fraction of interstitial fibrosis
Cap/mm2 = Capillary density
ODD = Oxygen diffusion distance
MCSA = myocyte cross-sectional area MCP is a mixture of high molecular weight pectic fractions that bind to and inhibit galectin-3. LacNAc is a low molecular weight disaccharide that is also a well-characterized ligand of galectin-3. MCP and LacNAc are diverse members of carbohydrate compounds known to bind to and inhibit galectin-3. Microembolization-induced heart failure is galectin-3 dependent and MCP and LacNAc showed an equivalent beneficial response. A comparison chart of MCP and LacNAc is shown in FIG. 2.

Therefore, embodiments disclosed herein indicate that therapy with a specific inhibitor of galectin-3 will improve left ventricular function and relieve symptoms of congestive HF in subjects with diastolic HF. Furthermore, embodiments disclosed herein indicate that chronic therapy with a specific inhibitor of galectin-3 may improve left ventricular function and relieve symptoms of congestive HF in patients with systolic HF.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for treating heart failure with preserved ejection fraction (HFpEF) in a subject in need thereof, the subject having a left ventricular ejection fraction of greater than 45% before treatment, the method comprising:
   administering a therapeutically effective amount of N-acetyl-D-lactosamine (LacNAc) to the subject.

2. The method of claim 1, wherein the subject has a left ventricle of reduced size compared with a control subject.

3. The method of claim 1, wherein the subject has reduced left ventricular end-systolic and end-diastolic volumes compared with a control subject.

4. The method of claim 1, wherein administering N-acetyl-D-lactosamine (LacNAc) reduces interstitial fibrosis in the subject compared to before treatment.

5. The method of claim 4, wherein interstitial fibrosis is reduced by at least 50%.

6. The method of claim 1, wherein administering N-acetyl-D-lactosamine (LacNAc) increases left ventricular size in the subject compared to before treatment.

7. The method of claim 1, wherein administering N-acetyl-D-lactosamine (LacNAc) increases left ventricular end-systolic and end-diastolic volumes in the subject compared to before treatment.

8. The method of claim 1, wherein administering N-acetyl-D-lactosamine (LacNAc) increases left ventricular ejection fraction in the subject compared to before treatment.

9. The method of claim 1, wherein administering N-acetyl-D-lactosamine (LacNAc) increases E/A and Ei/Ai ratios in the subject compared to before treatment.

* * * * *